United States Patent [19]

LaFontaine et al.

[11] Patent Number: 5,407,424
[45] Date of Patent: Apr. 18, 1995

[54] ANGIOPLASTY PERFUSION PUMP

[75] Inventors: Daniel M. LaFontaine, Plymouth; Thomas J. Holman, Minneapolis; Daniel O. Adams, Orono, all of Minn.

[73] Assignee: SciMed Life Systems, Inc., Maple Grove, Minn.

[21] Appl. No.: 22,048

[22] Filed: Feb. 24, 1993

[51] Int. Cl.$^6$ .............................................. A61M 37/00
[52] U.S. Cl. ......................................... 604/4; 417/534
[58] Field of Search .................... 417/534, 536; 604/4, 604/7, 8

[56] References Cited

U.S. PATENT DOCUMENTS

| | | |
|---|---|---|
| 167,366 | 8/1875 | Tyler . |
| 407,934 | 7/1889 | Kirkwood . |
| 443,083 | 12/1890 | Bartsch . |
| 458,774 | 9/1891 | Lottridge . |
| 497,250 | 5/1893 | Oliver . |
| 636,118 | 10/1899 | Deknatel et al. . |
| 658,325 | 9/1900 | Stukes et al. . |
| 679,454 | 7/1901 | Conner . |
| 717,084 | 12/1902 | Denham . |
| 930,312 | 8/1909 | Neveu . |
| 1,029,476 | 6/1912 | Peters . |
| 1,128,089 | 2/1915 | Astrom . |
| 1,170,661 | 2/1916 | Myers . |
| 1,223,243 | 4/1917 | Bessesen . |
| 1,248,230 | 11/1917 | Williams . |
| 1,275,440 | 8/1918 | Johnson . |
| 1,332,293 | 3/1920 | Hanger . |
| 1,390,559 | 9/1921 | Huntley . |
| 1,392,928 | 10/1921 | Foss . |
| 1,527,226 | 2/1925 | Rollins . |
| 1,777,195 | 9/1930 | Cairncross . |
| 1,806,268 | 5/1931 | Schulze . |
| 1,851,802 | 3/1932 | Boone . |
| 1,880,494 | 10/1932 | Sandage . |
| 1,930,731 | 10/1933 | Thompson . |
| 1,946,559 | 2/1934 | Weiskopf ............... 221/103 |
| 2,018,144 | 10/1935 | Mesinger . |
| 2,057,901 | 10/1936 | Moore .................. 128/214 |
| 2,077,774 | 4/1937 | Rudder . |
| 2,290,829 | 7/1942 | Edwards . |
| 2,338,419 | 1/1944 | Forrest et al. ........... 210/167 |
| 2,625,115 | 1/1953 | Maloney ................ 417/534 |
| 2,702,006 | 2/1955 | Bachert . |
| 2,972,960 | 2/1961 | Philip . |
| 2,989,227 | 6/1961 | Statham . |
| 3,039,399 | 6/1962 | Everett . |
| 3,083,648 | 4/1963 | Putman . |
| 3,180,096 | 4/1965 | Peterson . |
| 3,207,083 | 9/1965 | Lohry et al. . |
| 3,212,280 | 10/1965 | Thomas et al. . |
| 3,279,391 | 10/1966 | Masciopinto . |
| 3,398,743 | 8/1968 | Shalit . |
| 3,422,765 | 1/1969 | Schoch . |
| 3,456,648 | 7/1969 | Lee et al. . |
| 3,470,823 | 10/1969 | Seeger . |
| 3,478,956 | 11/1969 | Gosha . |
| 3,612,731 | 10/1971 | Tanemoto . |
| 3,692,438 | 9/1972 | Schapel . |
| 3,812,854 | 5/1974 | Michaels et al. . |
| 3,817,248 | 6/1974 | Buckles et al. . |
| 3,818,907 | 6/1974 | Walton . |
| 3,831,600 | 8/1974 | Yum et al. . |
| 3,840,009 | 10/1974 | Michaels et al. . |
| 3,895,631 | 7/1975 | Buckles et al. . |
| 3,990,816 | 11/1976 | Kohler et al. . |
| 3,993,069 | 11/1976 | Buckles et al. . |
| 3,994,294 | 11/1976 | Knute . |

(List continued on next page.)

FOREIGN PATENT DOCUMENTS 1170532  7/1984  Canada .

(List continued on next page.)

Primary Examiner—Richard E. Gluck
Attorney, Agent, or Firm—Nawrocki, Rooney & Sivertson

[57] ABSTRACT

A double acting piston blood pump having distal and proximal manifolds that are connected by a cylinder having a piston reciprocating therein and dividing the cylinder into a proximal and distal chambers. The manifolds have chambers that are in fluid communication with the distal and proximal chambers of the cylinder and one way valves for controlling fluid flow from and to the cylinder chambers.

22 Claims, 3 Drawing Sheets

U.S. PATENT DOCUMENTS

| | | |
|---|---|---|
| 4,028,017 | 6/1977 | Kobiske . |
| 4,030,495 | 6/1977 | Virag . |
| 4,054,137 | 10/1977 | Lee et al. . |
| 4,065,230 | 12/1977 | Gezari . |
| 4,082,095 | 4/1978 | Mendelson et al. . |
| 4,089,634 | 5/1978 | Sylvest . |
| 4,116,115 | 9/1978 | Gross et al. . |
| 4,140,117 | 2/1979 | Buckles et al. . |
| 4,140,118 | 2/1979 | Jassawalla . |
| 4,162,616 | 7/1979 | Hayashida . |
| 4,199,307 | 4/1980 | Jassawalla . |
| 4,201,207 | 5/1980 | Buckles et al. . |
| 4,236,880 | 12/1980 | Archibald . |
| 4,301,811 | 11/1981 | Layton . |
| 4,326,025 | 4/1982 | Buckles et al. . |
| 4,326,510 | 4/1982 | Buckles . |
| 4,334,839 | 6/1982 | Flagg . |
| 4,336,800 | 6/1982 | Pastrone . |
| 4,396,385 | 8/1983 | Kelly et al. . |
| 4,399,099 | 8/1983 | Buckles . |
| 4,443,163 | 4/1984 | Gaither . |
| 4,453,931 | 6/1984 | Pastrone . |
| 4,480,969 | 11/1984 | Credle . |
| 4,494,447 | 1/1985 | Sisk . |
| 4,541,455 | 9/1985 | Hauser . |
| 4,603,593 | 8/1986 | Clegg . |
| 4,643,713 | 2/1987 | Viitala . |
| 4,662,868 | 5/1987 | Cambio . |
| 4,734,269 | 3/1988 | Clarke et al. . |
| 4,771,777 | 9/1988 | Horzewski . |
| 4,784,637 | 11/1988 | Ryder et al. . |
| 4,838,860 | 6/1989 | Groshong et al. . |
| 4,838,866 | 6/1989 | Marshall . |
| 4,842,581 | 6/1989 | Davis . |
| 4,865,525 | 9/1989 | Kern . |
| 4,872,866 | 10/1989 | Davis . |
| 4,976,690 | 12/1990 | Solar et al. . |
| 5,013,295 | 5/1991 | Dubroff ................................ 604/38 |
| 5,049,135 | 9/1991 | Davis . |
| 5,066,282 | 11/1991 | Wijay . |
| 5,076,769 | 12/1991 | Shao . |
| 5,092,844 | 3/1992 | Schwartz et al. . |
| 5,106,363 | 4/1992 | Nobuyoshi . |
| 5,106,500 | 4/1992 | Hembree et al. .................... 210/266 |
| 5,158,540 | 10/1992 | Wijay . |

FOREIGN PATENT DOCUMENTS

| | | |
|---|---|---|
| 15654 | 2/1912 | Denmark . |
| 1030140 | 6/1953 | France ................................ 417/534 |
| 1496147 | 12/1977 | United Kingdom . |
| 1496650 | 12/1977 | United Kingdom . |
| 1600749 | 10/1981 | United Kingdom . |
| WO81/01445 | 5/1981 | WIPO . |

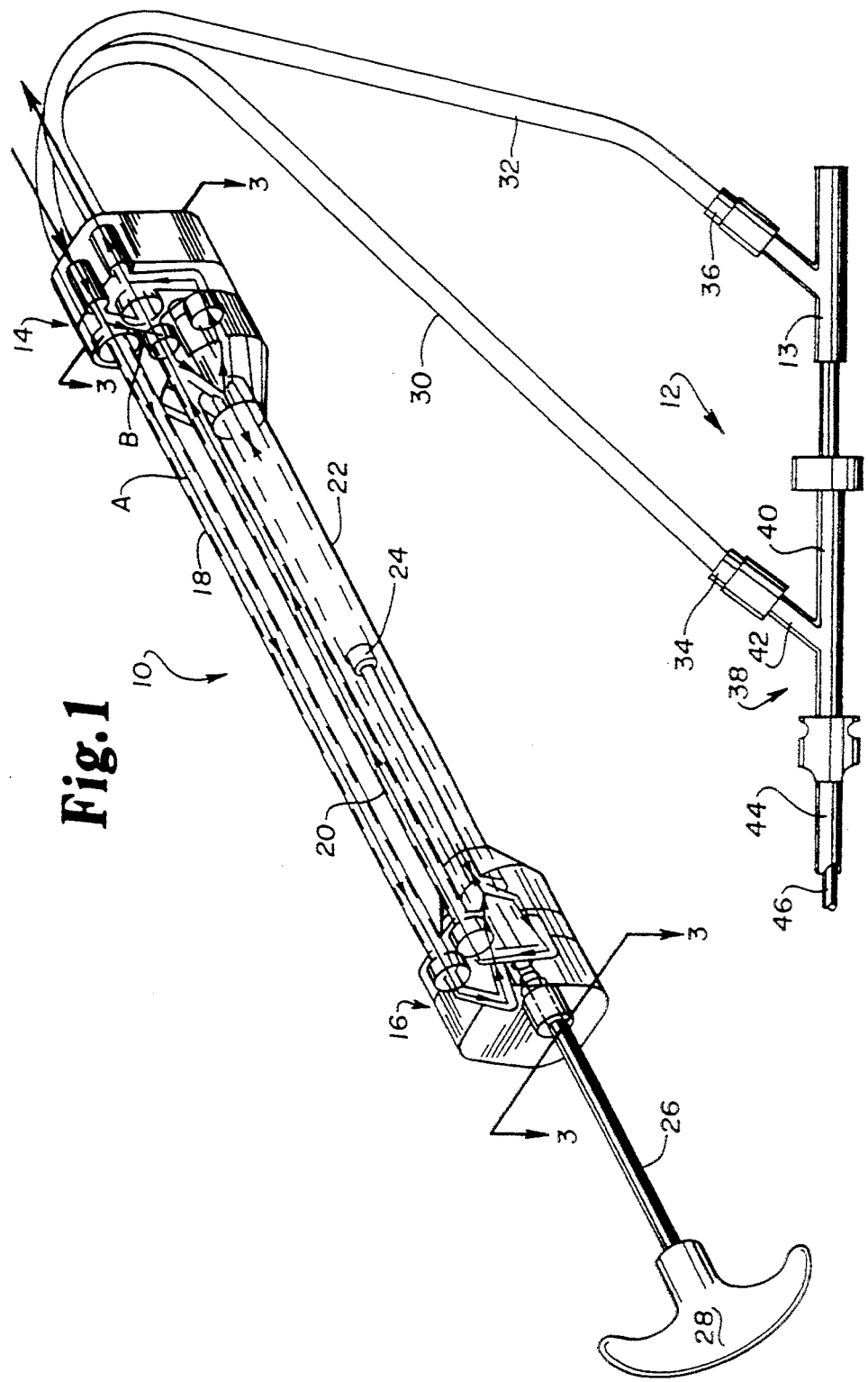

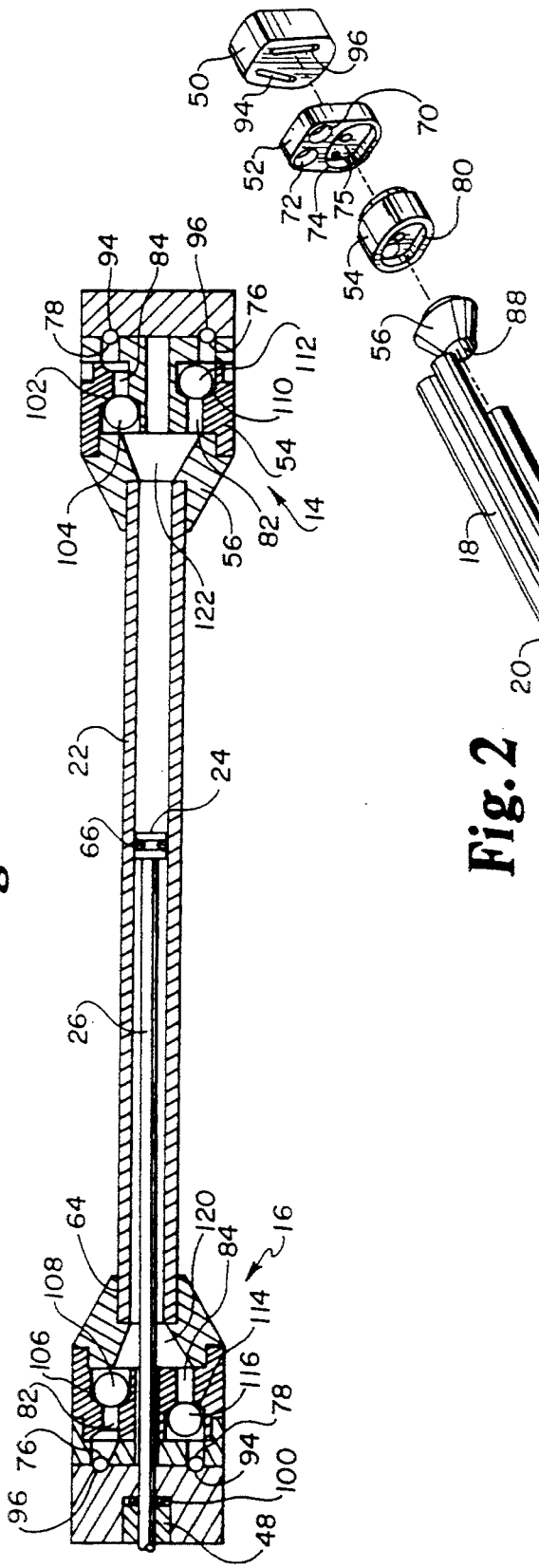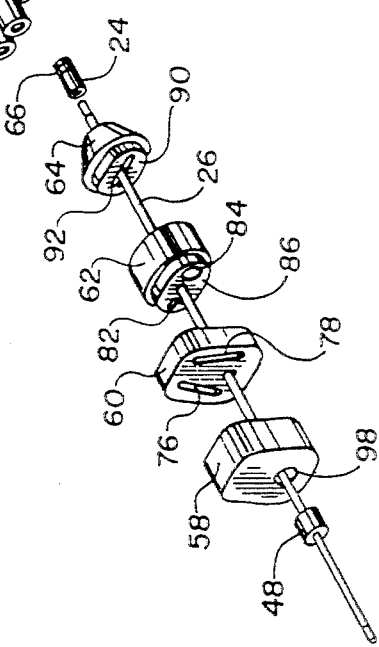

ANGIOPLASTY PERFUSION PUMP

BACKGROUND OF THE INVENTION

The field of the this invention is to perfusion pumps for use in angioplasty procedures.

Peristaltic pumps, used for pumping blood during open-heart surgery, do not have the capacity to generate pressures that are sufficient to force human blood through the relatively small lumens that are available in angioplasty balloon catheters.

U.S. Pat. No. 5,066,282 discloses a Positive Displacement Piston Driven Blood Pump for use during angioplasty. The invention of this patent is a single acting pump that includes an accumulation chamber having a membrane that functions to smooth out the pulsations of the single acting pump. The accumulation chamber must be filled with liquid and thus increases the total volume of fluid that is required to fill the system which adds to the weight and size of the pump. In addition to the pump a driver component is required and when combined this complex pump unit is relatively large and cumbersome and inconvenient for use in an operating room environment. In the preparation of a heart pump for use any air in the internal cavity of the pump must be removed to eliminate the possibility of pumping air into the patients blood stream. This preparation process becomes more difficult and time consuming as the volume of the internal cavity of the pump increases. In column 4, lines 9-14 of this patent, a double-acting arrangement is mentioned however such an arrangement is not described in full, clear and exact terms.

Because blood pumps are in direct contact with blood, in order to avoid spreading disease they cannot be reused and thus must be disposal. For this reason it is important that the cost of heart pumps be kept to a minimum.

Hemolysis, the breakdown of red blood cells, occurs normally when red blood cells lose their elasticity at the end of their life span. However, hemolysis may occur under many other circumstances such as when the blood is exposed to excessive shearing action as the result of greater than normal blood pressures, confining the blood flow to very small lumens and thus forcing the blood to flow at excessive flow rates and causing the blood to abruptly change its flow direction. Some hemolysis occurs when blood is forced to flow through the very small lumens available in an angioplasty catheter. The objective of this invention is to provide a simple blood perfusion pump, that can be manually powered with a minimum of effort, and can pump blood through an angioplasty catheter and balloon while minimizing hemolysis. In order to minimize hemolysis in the pump the conduits within the pump must be smooth, relatively large and shaped to accommodate directional changes in the blood flow path to thereby insure laminar flow and minimize turbulence and shear forces acting on the blood.

SUMMARY OF THE INVENTION

The present invention is directed to an apparatus that satisfies the need to provide a simple inexpensive blood perfusion pump, that can be manually powered with a minimum of effort, and can pump blood to an angioplasty catheter and balloon while minimizing hemolysis.

According to the invention a double acting piston blood pump having a barrel with proximal and distal ends is provided. A piston slidable in the barrel divides the barrel into distal and proximal chambers. The piston has a rod connected thereto, that extends out the proximal end of the barrel for reciprocating the piston. Distal and proximal manifolds are secured respectively to the distal and proximal ends of said barrel. The manifolds have chambers that are in fluid communication with the distal and proximal chambers of the barrel. Input and output conduits are formed in each of said manifolds that are in fluid communication with the chambers. One way valves are provided in the input conduits that will permit fluid flow into the chambers and prevent fluid flow out of the chambers. One way valves are provided in the output conduits that will permit fluid flow out of the chambers and prevent fluid flow into the chambers. Input and output ports are formed in the distal manifold for receiving and discharging blood. A conduit extends from the distal manifold to the proximal manifold for providing fluid communication from the blood inlet port of the distal manifold to the inlet of the proximal input conduit. A second conduit extends from the distal manifold to the proximal manifold for providing fluid communication from the blood outlet port of the distal manifold to the outlet of the proximal output conduit. A conduit is formed in the distal manifold for providing fluid communication between the blood input port and the inlet of the distal input conduit. A conduit in provided in the distal manifold providing fluid communication between the blood output port and the outlet of the distal output conduit.

To minimize hemolysis, when possible the conduits are in the form of round lumens having relatively large diameters, in the range of 0.032 to 0.250 of an inch. Conduits having a diameter of 0.090 of an inch are preferable.

The proximal and distal manifold are fabricated of four molded components that are assembled and then secured together by bonding or other fastening means. It is contemplated that the molded components could be fabricated with self locking and sealing features that would enable the components to be snapped together. As a result of assembling the manifolds from four components the internal chambers, conduits and valve seats can be made to precision and thereby avoid cavitation within the manifold. The one way ball valves included in the manifolds require that the ball be retained within a cage internally of the manifold. The fabrication of the manifolds from four components facilities the inclusion of one way valves in the manifolds. Of the four components that make up each manifold, three are identical and can be used in both manifolds. This of course greatly reduces the capital expenditure for molds and thus the cost of the perfusion pump.

During the priming process it is contemplated that the pump, pump cavities and tubing will be filled with saline solution. The pump will then be disconnected from the source of saline solution and connected to the patients blood supply. Upon actuation of the pump the saline solution contained in the pump cavities can be pumped into the patient. Although a small amount of saline solution is not harmful to the patient it is desirable to minimized the amount of saline fluid that is pumped into a patient. For this reason it is important to minimize the fluid capacity of the pump. For example a pump that does not require an accumulation chamber is preferable over one that does because it will require less liquid to fill it.

The pump of this invention has a stroke capacity in the range of 0.5 to 6.0 cubic centimeters per stroke, the preferred capacity is about 3 cubic centimeters per stroke. This capacity can be accomplished with a piston diameter in the range of 0.100 to 0.600 of an inch with a preferred diameter of 0.187 of an inch and a stroke length in the range of 2-12 inches and a preferred stroke of approximately 6 inches. The piston rod should have a diameter in the range of 0.060 to 0.125 and a preferred diameter of 0.090 inches. A pump having these limitations will be light and can be easily, confidently and comfortably handled by an operator for extended periods without expending unusual physical strength. A perfusion pump as disclosed herein has been found to require a force to be exerted on the handle in the range of 2 to 10 pounds. With the application of such a force the perfusion pump has developed pressures in excess of 250 pounds per square inch.

BRIEF DESCRIPTION OF THE DRAWINGS

FIG. 1 is perspective view of the perfusion pump connected to a catheter manifold assembly, showing the flow path through the pump.

FIG. 2 is an exploded view of the components that make up the perfusion pump.

FIG. 3 is a cross sectional view of the pump taken along lines 3—3 of FIG. 1.

DETAILED DESCRIPTION OF THE INVENTION

Figure 4:
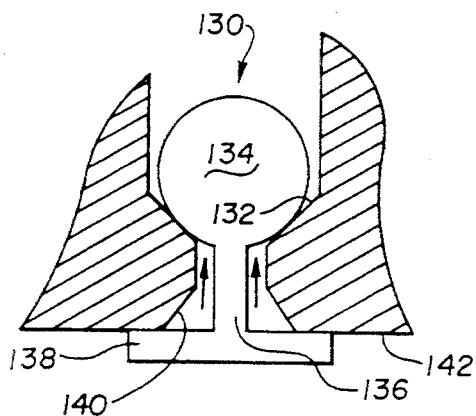
FIG. 4 is a cross section view of the preferred embodiment of the one way valve.

FIG. 1 discloses the perfusion pump 10 connected to an catheter manifold assembly 12. In this illustration some of the internal cavities and conduits and of the distal manifold 14, proximal manifold 16 and the piston 24 are shown as they may be seen if the components of the perfusion pump 10 were made of a clear plastic material. Also, lines with arrows have been included in FIG. 1 to trace the pathways that blood follows through the pump.

In the following discussion of FIG. 1 the check valves within the proximal and distal manifolds will not be mentioned since they are not seen in this illustration. The check valves will be fully discussed subsequently. Blood enters the perfusion pump 10 through the swivel luer 34 and travels through inlet tube 30 to the distal manifold 14. Blood flowing into distal manifold 14 can follow either pathway A or pathway B. When blood follows pathway A it leaves distal manifold 14 and flows through upper tubing 18 to the proximal manifold 16. When the piston 24 is moved in the distal direction blood following pathway A flows from the proximal manifold 16 into the proximal end of barrel or cylinder 22. When the piston 24 is moved in the proximal direction, by pulling on handle 28, flow is reversed and blood flows out the proximal end of barrel or cylinder 22 into the proximal manifold 16 and then into the upper tubing 20 which leads into distal manifold 14. This stream of blood then flows out of distal manifold 14 into outlet tube 32 and swivel luer 36.

The inlet and outlet tubes 32 and 34 should be made from compliant material such as reinforced vinyl hose. It is important that tubes 32 and 34 be made from a material that will permit a small amount of expansion and contraction corresponding to the pulsation of the pump. This expansion and contraction functions to smooth out the peaks and valleys in the pulses.

The above discussed movement of piston 24 in the proximal direction also created a pathway B flow of blood from inlet tube 30 into and through distal manifold 14 and then into the distal end of barrel or cylinder 22.

When piston 24 is forced to move distally, by actuation of the handle 28, blood is forced out of the distal end of barrel or cylinder 22 into distal manifold 14 and then through outlet tube 32. In some situations a thrombosis filter or a bubble trap or both could be inserted in outlet tube 32 to insure that thrombosis or air is not pumped into the patient.

The balloon catheter 13 is of the type that has a guide wire lumen that extends its entire length. Reference may be made to the U.S. Patent to Solar et al, U.S. Pat. No. 4,976,690 for a detailed disclosure of a balloon catheter of this type. When the angioplasty balloon is located over the stenoses the guide wire can be removed and the guide wire lumen can then be used to pump blood through the balloon into the vessel beyond the stenoses. The balloon catheter 13 extends through the mainport 40 of a Y-adapter 38 and out its distal end. A guide catheter 44 is connected to the distal end of the Y-adapter 38 and is inserted percutaneously into the patients vessel. The inside diameter of the guide catheter 44 is larger than the outside diameter of the balloon catheter's outer shaft 46, thus forming a coaxial lumen therebetween. The distal end of the guide catheter 44 is open and blood from the patients can flow in the proximal direction through the coaxial lumen. This blood flow from the patient flows into the Y-adapter 38 and out its sideport 42. Swivel luer 34 and inlet tube 30 are connected to sideport 42 and the blood stream from the patient thus flows through the Y-adapter 38 into the perfusion pump 10. As the patients blood flows through the perfusion pump 10 its pressure is increased and it exits the perfusion pump 10 at a sufficiently elevated pressure to flow through the small guide wire lumen of the balloon catheter 12.

FIG. 2 is an exploded view of the perfusion pump 10 showing the component parts separated from each other along the longitudinal axis of the pump. In this view internal chambers and conduits of the component parts are visible and their structure and function will be made clear in the following discussion.

When the perfusion pump 10 is assembled the distal splitter manifold 50, distal intermediate manifold 52, distal check manifold 54 and distal Y-manifold 56 are nested together and secured to each other by bonding or other connecting means. It should be noted that since pressurized fluid will be flowing through the cavities formed by this assembly of components the connection between the components must act to seal fluid flow between the components. It is also important that air not be permitted to enter the cavities in the perfusion pump 10 between the components. Although, not illustrated it is contemplated that self locking connecting means could be molded into the component parts such that they could snap together in the assembly process. The above remarks regarding the assembly of the distal component parts that make up distal manifold 14 apply equally to the proximal end manifold 58, proximal intermediate manifold 60, proximal check manifold 62 and proximal Y-manifold 64 of the proximal manifold 16. The component parts should be molded from a light strong material such as polycarbonate.

The piston 24 has a groove cut in its outer cylindrical surface for receipt of an o-ring 66. The o-ring 66 provides a liquid seal between the piston 24 and the inner wall of the barrel or cylinder 22 so that when the piston 24 reciprocates in barrel or cylinder 22 fluid will not flow past piston 24.

It should be understood that distal intermediate manifold 52 and proximal intermediate manifold 60 are identical but face in opposite directions. As a result both ends of this identical component can be seen in FIG. 2. Referring first to the end of this component that is seen when looking at distal intermediate manifold 52. There are a pair of tubing seats 70 and 72 that extend partially through the component. At the base of these tubing seats there are smaller diameter openings (not seen) that extend through the remainder of the component. In the lower half of the component there is an oval shaped opening 74 that extends partially through the component. There are a pair of small diameter openings 75 that extend from the bottom of the oval shaped opening 74 through the remainder of the component. On the end seen when viewing proximal intermediate manifold 60 a pair of downwardly diverging grooves 76 and 78 are seen. These grooves 76 and 78 have a semicircular cross section. The upper small diameter openings that open into tubing seats 70 and 72 also open into the upper ends of grooves 76 and 78 and the lower small diameter openings 75 open into the lower ends of grooves 76 and 78. The distal ends of upper tubing 18 and 20 are received in the tubing seats 70 and 72 of distal intermediate manifold 52. The proximal ends of upper tubing 18 and 20 are received in the tubing seats 70 and 72 of proximal intermediate manifold 60. The upper tubing 18 and 20 should be made from material such as acrylic tubing.

The distal check manifold 54 and proximal check manifold 62 are also identical and since they are turned to face each other both end faces are visible in FIG. 2. The end face of distal check manifold 54 seen in FIG. 2 has an oval shaped opening 80 formed therein. Two check valve conduits 82 and 84, visible when viewing proximal intermediate manifold 60, extend from the bottom of oval shaped opening 80 through the remainder of the component. On the face seen when viewing proximal check manifold 62 there is an oval shaped extension 86. The check valve conduits 82 and 84 can be seen in the face of extension 86. It should be noted that oval shaped extensions 86 are received in the oval shaped openings 74 formed in distal intermediate manifold 52 and proximal intermediate manifold 60.

The distal Y-manifold 56 and proximal Y-manifold 64 are identical and thus both faces of this component are visible in FIG. 2. In the visible face of distal Y-manifold 56 there is a cylinder seat 88. In the face of proximal Y-manifold 64 that is seen there is an oval shaped extension 90 that has a slot 92 formed therein. Both ends of slot 92 communicate with cylinder seat 88.

The proximal and distal ends of the barrel or cylinder 22 are received in the cylinder seats 88. Thus the distal manifold 14 and proximal manifold 16 are connected by barrel or cylinder 22 and upper tubing 20 and 22.

The distal splitter manifold 50 and proximal end manifold 58 are similar but not identical. In the visible face of distal splitter manifold 50 there is a pair of downwardly diverging groves 94 and 96, that have semicircular cross sections. Identical groves 94 and 96 are formed in the face of proximal end manifold 58 that is not visible in FIG. 2. Groves 94 and 96 mate with groves 76 and 78 formed in distal intermediate manifold 52 and proximal intermediate manifold 60 such that together they form conduits having circular cross sections. In the face of distal splitter manifold 50 that is not visible there are connectors for inlet tube 30 and outlet tube 32. These connectors are aligned with the upper ends of groves 94 and 96. In the visible face of proximal end manifold 58 there is an opening 98 from which the rod 26 extends. The opening 98 is larger in diameter than rod 26 and the back ring 48 is received in this space. The back ring 48 functions to provide a seal for the reciprocating rod 26.

FIG. 3 is a cross sectional view of the perfusion pump 10 taken along lines 3—3 of FIG. 1. This cross sectional view cuts through the valve conduits 82 and 84 that are formed in distal check manifold 54 and proximal check manifold 62. As can be seen in FIG. 3 the check valve conduit 84 of distal check manifold 54 functions as an input check valve. The input valve seat 102 is opened and closed by the ball valve 104. As can be seen in this view a portion of distal Y-manifold 56 cooperates with the valve seat 102 to form a cage that retains the ball valve 104.

The check valve conduit 82 of distal check manifold 54 functions as an output valve having a output valve seat 110 and a ball valve 112. A portion of the oval shaped opening 74 formed in distal intermediate manifold 52 cooperates with valve seat 110 to form a cage for retaining the ball valve 112.

The check valve conduit 82 in proximal check manifold 62 functions as an inlet valve having a input valve seat 106 and a ball valve 108. A portion of proximal Y-manifold 64 cooperates with the input valve seat 106 to form a cage for retaining the ball valve 108.

The check valve conduit 84 in proximal check manifold 62 functions as an outlet valve having a output valve seat 114 and a ball valve 116. The bottom of the oval shaped opening 74 formed in proximal intermediate manifold 60 cooperates with output valve seat 114 to form a cage to retain ball valve 116.

The piston 24 and connected rod 26 are also visible in this view. The o-ring 66 that is carried in a grove formed in the cylindrical surface of piston 24 provides a seal for piston 24 to prevent fluid flow past the piston 24. At the proximal end of the rod 26 the back ring 48 and an o-ring 100 function to seal the rod 26 to prevent liquid leakage at this point.

The following discussion of operation of perfusion pump 10 should be read with reference to FIGS. 1-3 and will be more specific than the earlier, especially with respect to the discussion of the one way check valves. Blood enters the perfusion pump 10 through the swivel luer 34 and travels through inlet tube 30 to the distal manifold 14. Blood flowing into distal manifold 14 can follow either pathway A or pathway B. When blood follows pathway A it leaves distal manifold 14 and flows through upper tubing 18 to the proximal manifold 16. The fluid flows down the conduit formed by groves 76 and 96. The flow then enters inlet check valve conduit 82, forces ball valve 108 off valve seat 106, and into a chamber 120 formed in proximal Y-manifold 64. When the piston 24 is moved in the distal direction blood following pathway A flows from chamber 120 into the proximal end of barrel or cylinder 22. When the piston 24 is moved in the proximal direction, by pulling on handle 28, flow is reversed and blood flows out the proximal end of barrel or cylinder 22 into chamber 120 and then into output check valve conduit 84 where it forces ball valve 116 off valve seat 114. The fluid then flows up the conduit formed by channels 94 and 78 and then into upper tubing 20 which leads into distal manifold 14. This stream of blood then flows through the conduit in distal intermediated manifold 52 and distal splitter manifold 50 into the outlet tube 32.

The movement of piston 24 in the proximal direction also created a pathway B flow of blood from inlet tube 30 down the conduit formed by groves 94 and 78 into the inlet conduit 84 where it forces ball valve 104 off valve seat 102 and then into chamber 122 which is formed in distal Y-manifold 56. The fluid then flows from chamber 122 into the distal end of barrel or cylinder 22.

When piston 24 is forced to move distally, by actuation of the handle 28, blood is forced out of the distal end of barrel or cylinder 22 into chamber 122, up the conduit formed by grooves 96 and 76 and then out through outlet tube 32.

The one way check valves, illustrated in FIG. 3, are all of the type in which a ball valve is restrained in a cage having a valve seat. When there is fluid flow through the cage toward the valve seat the ball valve seats on the valve seat and flow through the cage is stopped. When flow is in the opposite direction it forces the ball valve off the valve seat and permits fluid flow through the cage. In FIG. 3 there is no structural means, such as a spring, exerting a pressure on the ball valve in the direction toward the valve seat. Thus in this embodiment, when there is no flow through the cage, there is no assurance that the ball valve is resting on the valve seat.

Figure 5:
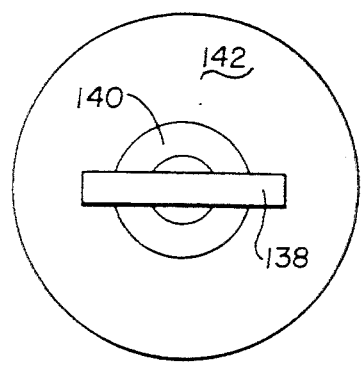
FIG. 5 is a bottom view of the one way valve show in FIG. 4.

In FIGS. 4 and 5 another embodiment of a one way valve is illustrated. This embodiment represents the preferred embodiment. FIG. 4, is a cross section view through the element forming the valve conduit 130 and the valve seat 132. The ball valve 134, which is not shown in cross section, includes a T-shaped restrainer comprising a stem 136 and a cross bar 138. The stem 136 is dimensioned such that at equilibrium the ball valve 136 is resting on valve seat 132 and is restrained from movement away therefrom. This one way check valve is designed such that when there is no flow through the valve conduit 130 there is a pre-load force on ball valve 134. This pre-load force should be in the range of 1-100 grams and preferable about 5 grams. The ball valve 136 with its integral T-shaped restrainer is installed by pinching the free ends of cross bar 138 together such that they can pass through the restricted portion of valve conduit 130. The cross bar will spring back into its original shape, as seen in FIG. 4, after it is in place. The inlet side of the conduit 130 is flared at 140 to provide a large entrance into the conduit 130. The cross bar 138 extends across the flared inlet opening into conduit 130 and is seated on a flat surface 142. When there is fluid flow in the direction of the arrows in FIG. 4, the cross bar 138 bows up into the flared opening 140 of the inlet conduit thus permitting ball valve 134 to moved off valve seat 132 and allow flow through the one way valve. FIG. 5 is a bottom view of FIG. 4 and it illustrates the relationships between the components of this one way valve.

Figure 6:
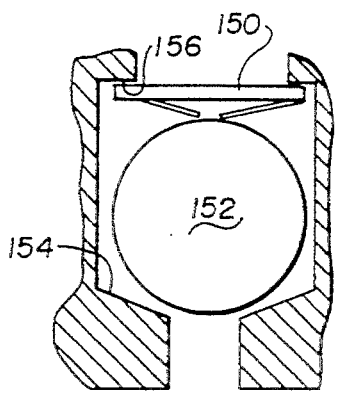
FIG. 6 is a cross sectional view of another embodiment of a one way valve.

FIG. 6 illustrates another embodiment of one way valve that could be used in the perfusion pump. In this embodiment there is a spring 150, that could be stamped from sheet material, in engagement with the ball valve 152. Spring 150 exerts a pre-load force on ball valve 152 causing it to set on valve seat 154. When this pre-load force is overcome the one way valve opens and fluid flows past the ball valve 152. It is noted that this embodiment requires a reaction surface 156 for spring 150. The spring 150 of this embodiment has a pair of cantilever tabs that are permanently bent in the direction toward the ball valve. The spring 150 bears against reaction surface 156 and the free ends of the cantilevered tabs contact the ball valve 152.

Figure 7:
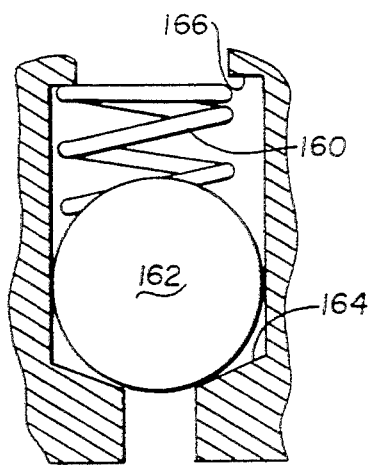
FIG. 7 is a cross sectional view of another embodiment of a one way valve.

FIG. 7 illustrates still another embodiment of a one way valve that could be used in the perfusion pump. In this embodiment there is a coil spring 160 in engagement with the ball valve 162 forcing it into contact with the valve seat 164. In this embodiment one end of coil spring 160 engages a reaction surface 166 and the other end engages ball valve 160. This causes a pre-load force to be exerted on ball valve in the direction of valve seat 164.

Although the illustrations of check valves included in this application all have spherical shaped valves it should be understood that the valve could have an ellipsoid, oval or other similar shape. Also it should be understood that other common types of one way valves such a rubber flap valve could be used as well as a ball type valve.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A double acting piston blood pump comprising a barrel having proximal and distal ends, a piston slidable in said barrel and dividing said barrel into distal and proximal chambers;

a rod connected to said piston and extending out the proximal end of said barrel;

distal and proximal manifolds secured respectively to the distal and proximal ends of said barrel;

manifold chambers formed in said distal and proximal manifolds that are in fluid communication with said distal and proximal chambers of said barrel;

input and output conduits formed in each of said manifolds, said input and output conduits each having an inlet and an outlet, wherein said outlets of said input conduits and said inlets of said output conduits are in fluid communication with said manifold chambers;

one way valves in said input conduits that will permit fluid flow into said manifold chambers and prevent fluid flow out of said manifold chambers;

one way valves in said output conduits that will permit fluid flow out of said manifold chambers and prevent fluid flow into said manifold chambers;

blood input and output ports formed in said distal manifold;

a first conduit extending from said distal manifold to said proximal manifold that provides fluid communication from said blood inlet port of said distal manifold to the inlet of said proximal input conduit;

a second conduit extending from said distal manifold to said proximal manifold that provides fluid communication from said blood outlet port of said distal manifold to the outlet of said proximal output conduit;

a conduit in said distal manifold providing fluid communication between said blood output port and the outlet of said distal output conduit.

2. The invention as set forth in claim 1 wherein said first and second conduits are in the form of smooth lumens having a diameter in the range of 0.032 of an inch to 0.250 of an inch.

3. The invention as set forth in claim 1 wherein the pump will displace in the range of 0.5 to 6.0 cubic centimeters of fluid per stroke.

4. The invention as set forth in claim 1 wherein the piston has a diameter in the range of 0.100 of an inch to 0.600 of an inch.

5. The invention as set forth in claim 1 wherein said pump has a stroke in the range of 2 to 12 inches.

6. The invention as set forth in claim 1 wherein said one way valves include ball valves having a diameter in the range of 0.032 to 0.250 inches.

7. The invention as set forth in claim 1 wherein said input and output ports of said pump are connected to a catheter manifold assembly by input and output tubes.

8. The invention as set forth in claim 7 wherein said input and output tubes are made from compliant material that will expand and contract in response to the pump pulsations.

9. The invention as set forth in claim 7 wherein said input and output tubes have a length in the range of 6 to 36 inches.

10. The invention as set forth in claim 1 wherein said one way valves include a check valve conduit, a ball valve including a ball portion having a T-shaped retainer extending radially therefrom, said check valve conduit having a large diameter section for reception of said ball portion of said ball valve, a small diameter section, a valve seat between said large and small diameter sections and a surface generally normal to the axis of said check valve conduit at the end of said small diameter section, said T-shaped retainer including a stem that extends radially from the surface of said ball portion, said stem having a free end portion, a cross bar connected at its mid portion to the free end portion of said stem, the length of said stem being such that when said ball portion is resting on said valve seat the ends of said cross bar are resting on said surface generally normal to the axis of said check valve conduit and said cross bar is bent such that it exerts a pre-load pressure on the ball portion toward said valve seat.

11. A double acting piston pump of the type having a barrel with proximal and distal ends, a piston slidable in said barrel and dividing said barrel into distal and proximal chambers, distal and proximal manifolds secured respectively to the distal and proximal ends of said barrel, the improvement comprising.:

the distal and proximal manifold having manifold chambers, input and output conduits and valve seats formed therein that will cause said piston to pump blood when forced to move in either direction, the proximal and distal manifolds being fabricated from a plurality of components that are assembled together to form the manifolds, said plurality of components for each manifold including a Y-manifold having a first end in fluid communication with said barrel and a second end with a fluid chamber formed therein, a check manifold having a first end affixed to and in fluid communication with said chamber of said second end of said Y-manifold and a second end, said check manifold having a first check valve seat formed therein and a first check valve member operatively seated thereon and a second check valve seat formed therein and a second check valve member operatively seated thereon to form a pair of check valve assemblies, one of said assemblies which prevents flow in a first direction the other of which prevents flow in an opposing direction through said check manifolds, an intermediate manifold having a first end secured to the second end of said check manifold, said intermediate manifold having a second end in fluid communication with said input and output conduits, said Y-manifolds, said intermediate manifolds and said check manifolds being identical and interchangeable between the proximal and distal manifolds.

12. The invention as set forth in claim 11 wherein said conduits are in the form of smooth lumens having a diameter in the range of 0.032 of an inch to 0.250 of an inch.

13. The invention as set forth in claim 11 wherein the pump will displace 2–6 cubic centimeters of fluid per stroke.

14. The invention as set forth in claim 11 wherein the piston has a diameter in the range of 0.100 of an inch to 0.600 of an inch.

15. The invention as set forth in claim 11 wherein the piston has a diameter in the range of 0.100 of an inch to 0.600 of an inch.

16. The invention as set forth in claim 11 in which the Y-manifold has a Y-shaped chamber formed therein.

17. The invention as set forth in claim 11 in which the proximal and distal manifolds each include a conduits component that receives the conduits that provide fluid communication between the proximal and distal manifolds, and further in which the conduit components are identical and interchangeable.

18. The invention as set forth in claim 16 in which the proximal and distal manifolds each include a conduits component that receives the conduits that provide fluid communication between the proximal and distal manifolds, and further in which the conduit components are identical and interchangeable.

19. The invention as set forth in claim 11 wherein said one way valves include ball valves having a diameter in the range of 0.032 to 0.250 inches.

20. The invention as set forth in claim 11 wherein said input and output ports of said pump are connected to a catheter manifold assembly by input and output tubes.

21. The invention as set forth in claim 20 wherein said input and output tubes are made from compliant material that will expand and contract in response to the pump pulsations.

22. The invention as set forth in claim 20 wherein said input and output tubes have a length in the range of 6 to 36 inches.

* * * * *